(12) United States Patent
Porat

(10) Patent No.: US 7,755,072 B2
(45) Date of Patent: Jul. 13, 2010

(54) SYSTEM AND METHOD FOR THREE-DIMENSIONAL LOCATION OF INCLUSIONS IN A GEMSTONE

(76) Inventor: Zvi Porat, 1 Achim Israelit St., Petach Tikva 49223 (IL)

( * ) Notice: Subject to any disclaimer, the term of this patent is extended or adjusted under 35 U.S.C. 154(b) by 1203 days.

(21) Appl. No.: 10/944,898

(22) Filed: Sep. 21, 2004

(65) Prior Publication Data

US 2006/0062446 A1 Mar. 23, 2006

(51) Int. Cl.
*G01N 21/86* (2006.01)
*G06M 7/00* (2006.01)
*G01T 1/20* (2006.01)
*G01N 21/00* (2006.01)

(52) U.S. Cl. .............. 250/559.22; 250/221; 250/363.01; 356/30

(58) Field of Classification Search ............ 250/559.22, 250/559.23, 216, 221, 222.1, 330, 461.1, 250/461.2, 363.01, 363.02, 363.06, 559.4; 356/30, 601, 613, 244, 432; 125/30.01; 378/73
See application file for complete search history.

(56) References Cited

U.S. PATENT DOCUMENTS

| | | | | |
|---|---|---|---|---|
| 4,125,770 A | * | 11/1978 | Lang ........................... 378/74 |
| 4,417,564 A | * | 11/1983 | Lawrence et al. ........ 125/30.01 |
| 4,529,305 A | * | 7/1985 | Welford et al. ................ 356/30 |
| 5,351,117 A | * | 9/1994 | Stewart et al. ................ 356/30 |
| 5,811,817 A | * | 9/1998 | Ravich ....................... 250/372 |
| 5,835,205 A | * | 11/1998 | Hunter et al. ................. 356/30 |
| 6,567,156 B1 | * | 5/2003 | Kerner ......................... 356/30 |
| 6,603,103 B1 | * | 8/2003 | Ulrich et al. ................ 250/205 |
| 6,813,007 B2 | * | 11/2004 | Lapa et al. ..................... 356/30 |
| 2003/0107722 A1 | * | 6/2003 | Klingler ...................... 356/30 |
| 2004/0246464 A1 | * | 12/2004 | Sivovolenko ................ 356/30 |

FOREIGN PATENT DOCUMENTS

WO WO 03/070441 A1 2/2002
WO WO 02/46725 6/2002

* cited by examiner

*Primary Examiner*—Georgia Y Epps
*Assistant Examiner*—Don Williams
(74) *Attorney, Agent, or Firm*—Daniel J. Swirsky; AlphaPatent Associates Ltd.

(57) ABSTRACT

The present invention presents a non-destructive method and means of obtaining either the inner portion or the outer contour of a two-dimensional or three-dimensional model of the outer contours of a gemstone. The method comprising the steps of placing the gemstone on a holder such that the gemstone to be scanned is located in a radiation path comprising inter alia at least one emitter and at least one detector synchronized by a processor; radiating said gemstone by means of said emitter; detecting the emitted irradiation by means of said detector; processing said detection such that a two-dimensional in-scan of said gemstone is obtained by means of said processor; displacing the gemstone in respect to said emitter and said detector; repeating steps (b) through (e) for a plurality of predetermined displacements; and, if a three-dimensional model is required, integrating the obtained multiple two-dimensional in-scans into a three-dimensional model of the gemstone's outer contours; wherein the emitter is an irradiation delivery device, selected from a group consisting of either monochromatic or white light, UV or IR emitters; X-ray radiation source and/or collimator of the same; NMR, CT, NQR and/or MIR scatters; beta radiation emission devices; gamma radiation emission devices; laser beam cannons; photons cannons; microwave or RF emitters; sonic or ultrasonic emitters or any combination thereof.

23 Claims, 3 Drawing Sheets

Figure 2:
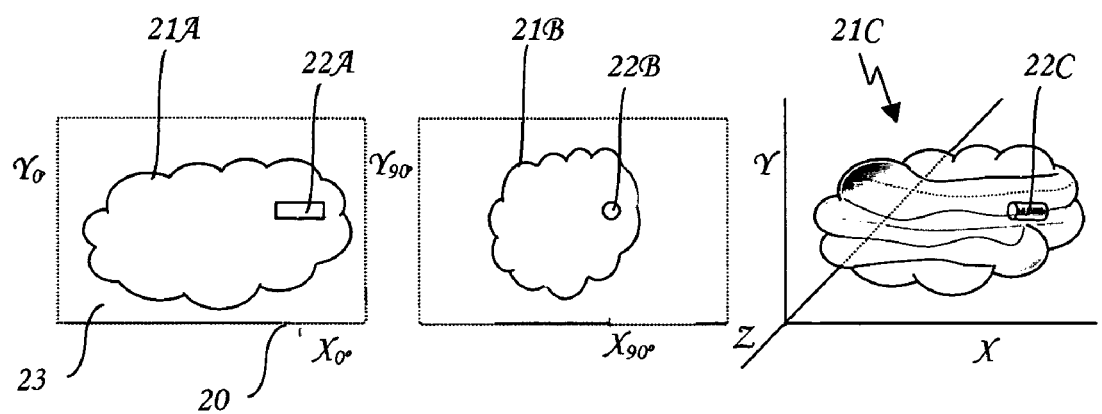

*Fig. 2A*   *Fig. 2B*   *Fig. 2C*

SYSTEM AND METHOD FOR THREE-DIMENSIONAL LOCATION OF INCLUSIONS IN A GEMSTONE

FIELD OF THE INVENTION

The present invention generally relates to a non-destructive analyzing system and to a method of three-dimensional location of inclusions in a gemstone.

BACKGROUND OF THE INVENTION

Natural gemstones and diamonds are rare and require skill and tedious processing efforts to draw out the full beauty from the rough stone. Various different shapes of polished gemstones may be obtained from the rough stone; thus that the cut, which utilize most of the stone in terms of weight, shape and clarity, is the most profitable one. Thus, in order to realize the full potential and maximize market value thereof, it is desirable to determine in advance the optimal finished gem, which can be cut from the untreated stone.

In automated gemstone imaging systems known in the art, the scanned gemstone is maneuvered to a 360 degrees circle by means of a rotating gemstone holder. The image provided by those techniques are obtained separately and only one half of the gemstone is usually photographed at one session. The gemstone is photographed approximately at 5-degrees intervals, resulting in about 36 to 90 images for both halves of a gemstone, a relatively long procedure taking up to 30 seconds. The images are used to create a three dimensional picture of the gemstone. The system works by use of sequential repeat commands such as (1) take a picture; (2) rotate 5 degrees; and (3) stop; and by repeating these commands until the gemstone has rotated 180 degrees.

Moreover, a number of computerized scanning systems have been adapted to examine gemstones and diamonds and to compare the shape of the stone with a variety of predetermined shapes in order to establish the best fit. In one type of scanning system, the stone is lit from the rear, providing a silhouette thereof, which is analyzed by the computer and compared with a number of silhouettes of finished stones. In a second type such as that disclosed in U.S. Pat. No. 4,417,564, the stone is scanned perpendicular to the axis, so as to permit the computer to provide a three-dimensional image of the stone.

Both types of scanning systems discussed above may be advantageous in detecting protrusions but useless or ineffective in case of reentrants or recesses in the stone, which remain invisible; this may result in incorrect decisions regarding the proper working of the stones.

In a third type of system, such as that described in IL Pat. 66292, a thin beam of light is projected onto the stone and moved relative to it. The point where the beam strikes the stone as viewed in a direction different from that from which the beam is projected. However, this method may suffer from inaccuracies in the reentrants measurements.

U.S. Pat. No. 6,567,156 discloses a fourth type of examining method comprising coating the gemstone with a removable diffusing coating and determining the silhouette of the gemstone in three dimensions. The method further includes structured light triangulation performed by using laser light to obtain an image of the surface of the gemstone.

Gemstone clarity is a measure of a gemstone's lack of internal flaws and impurities. A gemstone that is virtually free of interior or exterior inclusions is of the highest quality, for nothing interferes with the passage of light through the gemstone. As inclusions gravely degrade the finished stone's value, it is desirable to take them into account when optimizing the cut. However in many cases these inclusions are not visible or locatable until late stages of the polishing process, and thus cannot be avoided in advanced refining stages.

A manual method for determining inner inclusions is only partially provided by means of carving a small picking hole or window into the stone and probing through it, using an optical fiber or a stent, in the search for such inclusions. Clearly this method cannot map all inclusions potentially residing in the stone and further risks damaging the stone, in part or in whole In WO 02/46725 to Sivovlenko et al., a method and apparatus for locating inclusions in a diamond is disclosed, wherein said diamond is fixed on a holder and observed under a predetermined angle to obtain an image. A second measurement is carried out to obtain data to be calculated in a computer, either by a depth measurement, or by changing the direction of observation, in order to localize the inclusion with respect to the outer surface of said diamond.

It is thus acknowledged that there is no reference in the prior art that the inner portion of the gemstone, comprising potential inclusions are detected or located in a non-destructive means prior to the gemstone processing stages.

A cost-effective method and system for three-dimensional mapping of both the outer and inner surfaces of a gemstone, useful for optimizing yield, thus meets a long felt need.

SUMMARY OF THE INVENTION

It is thus in the scope of the present invention to provide a non-destructive method of obtaining the outer contours of a gemstone. This rapid and cost effective method comprises the steps of (a) placing the gemstone on a holder such that the gemstone to be scanned is located in a radiation path comprising inter alia at least one emitter and at least one detector synchronized by a processor; (b) radiating said gemstone by means of said emitter; (c) detecting the emitted irradiation by means of said detector; (d) processing said detection such that a two-dimensional in-scan of said gemstone is obtained by means of said processor; (e) displacing the gemstone in respect to said emitter and said detector. Steps (b) through (e) are repeated for a plurality of predetermined displacements, and the obtained multiple two-dimensional in-scans are integrated into a three-dimensional model of the gemstone.

The displacement is preferably provided by rotating the scanned gemstone by circulating the holder along a predetermined XY, XZ, YZ, and/or XYZ planes to a predetermined angle. For imaging the inner and/or outer portions of the gemstone, the gemstone is rotated in an overall rotation angle of about 45° to about 360° or more wherein images are taken in intervals of about 1° to about 10° or more. For imaging and or locating the inclusions, the gemstone is rotated in an overall rotation angle of about 45° to about 360° or more, wherein images are taken either in relatively large intervals, e.g., 3 to 8 images per overall rotation angle (e.g., intervals of 45° to 120°), in any predetermined intervals as function of the inclusion specific geometry or in small intervals, of about 1° to about 10° or more.

It is also in the scope of the present invention to provide a non-destructive method as defined above, especially adapted for obtaining a two dimensional (2D) and/or three-dimensional (3D) coordinated model of inclusions located in the inner and/or outer portion of a gemstone, by integrating the obtained multiple two-dimensional in-scans into a three-dimensional model of the inclusions of the gemstone.

It is further in the scope of the present invention to provide a non-destructive method as defined in any of the above, especially adapted for obtaining a three-dimensional coordinated model of inclusions located in the inner and/or outer portion of a gemstone in respect to the outer contour of the gemstone. This method integrates the multiple two-dimensional in-scans obtained into a comprehensive three-dimensional model of the inclusions and the outer contour of the gemstone.

Also provided hereinafter is an effective and retrievable method for identifying, analyzing and/or commercially evaluating a gemstone, by obtaining a three-dimensional coordinated model of the inclusions in respect to the outer contour of the gemstone, by one or more of the methods defined above.

It is still in the scope of the present invention to provide a non-destructive system for obtaining a three-dimensional coordinated model of a gemstone. This cost effective system comprises inter alia a holder adapted to carry the scanned diamond; at least one emitter adapted to radiate said gemstone; at least one detector adapted to detect the emitted irradiation targeted at the gemstone; a displacing means adapted to repeatedly displace said gemstone both in respect to said emitter and said detector, to a predetermined location; a processor adapted to process said detection such that a two-dimensional in-scan of said gemstone is obtained; and subsequently to integrate the obtained multiple two-dimensional in-scans into a three-dimensional model of the gemstone, wherein the obtained three-dimensional coordinated model is selected from the group consisting of the gemstone's outer contour; a model of either the inner or outer inclusions of the gemstone, if any; a comprehensive model of said inclusions in respect to said outer contour or any combination thereof.

BRIEF DESCRIPTION OF THE INVENTION

Figure 1:
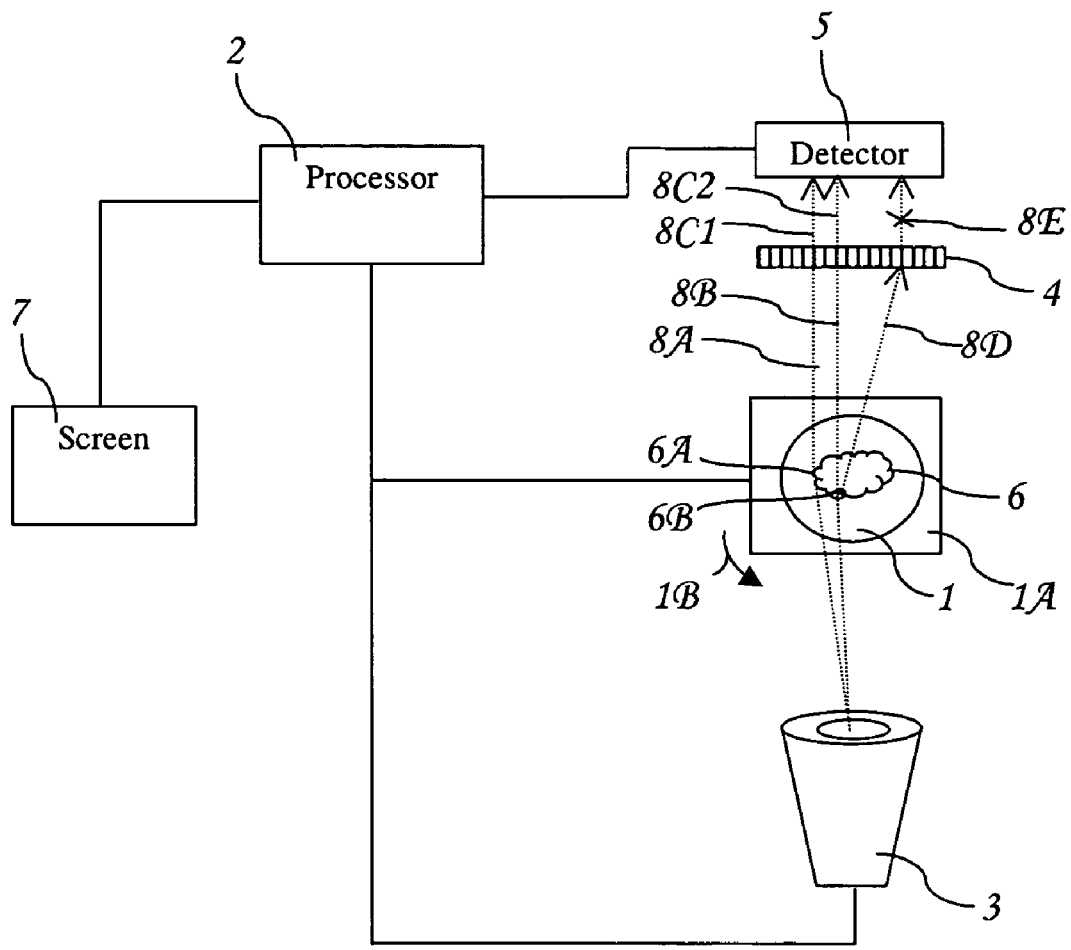
Figure 3:
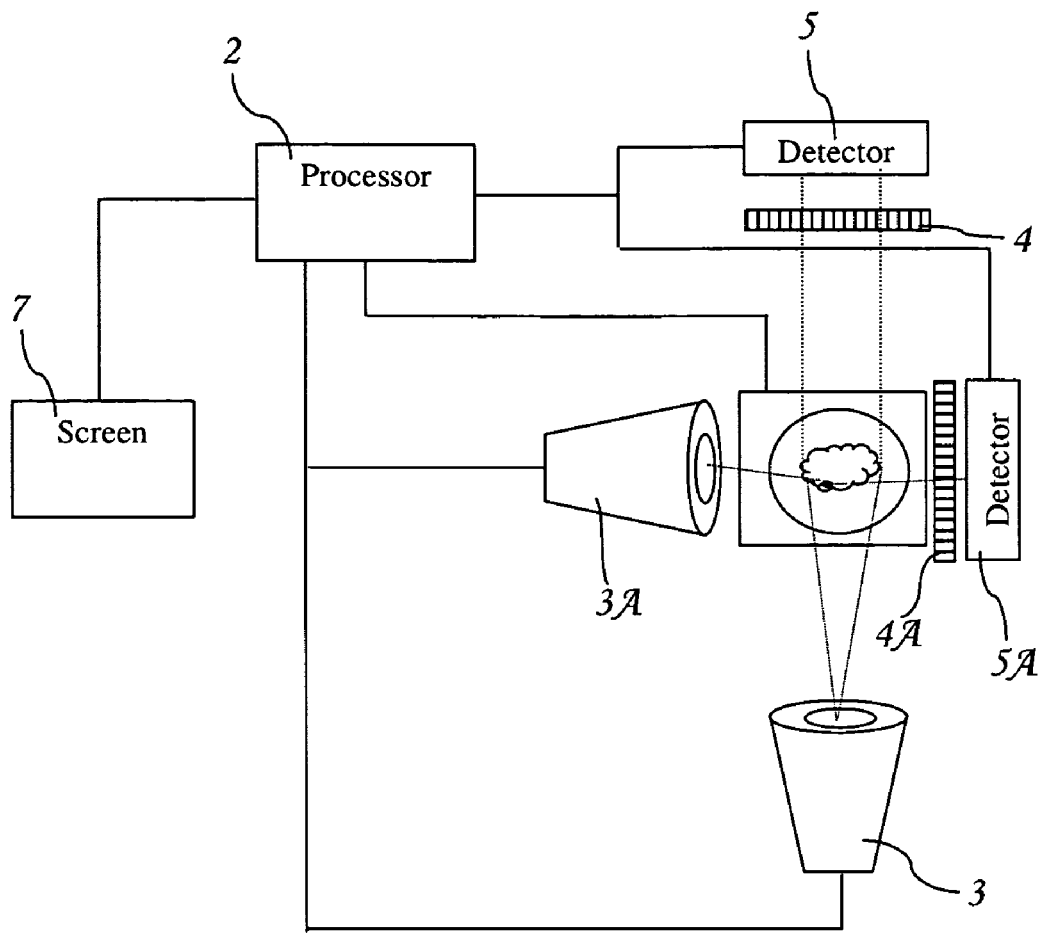

In order to understand the invention and to see how it may be implemented in practice, several embodiments will now be described, by way of non-limiting example only, with reference to the accompanying drawing, in which FIG. 1 schematically presents an imaging system for three-dimensional location of inclusions in a gemstone comprising a single set of emitter and etector;

FIGS. 2A-2C schematically present a scanned rough gemstone comprising a single tubular flaw made possible by means of the method defined in the present invention, wherein FIG. 2A and 2B are two dimensional diffractions of the stone at 0 and 90 degrees, and FIG. 2C is the corresponding calculated three dimensional image of the same, characterized by well defined XYZ coordinates of the external contour and inner inclusion; and, FIG. 3 FIG. 1 schematically presents an imaging system for location of inclusions in a gemstone comprising a multiple sets of emitters and detectors; here, one set is adapted to provide a 3D imaging the outer contour of the gemstone and a second set is adapted to provide either 2D or 3D mapping of the inclusions.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a non-destructive analyzing system and method of three-dimensional location of inclusions in a gemstone.

The term 'gemstone' refers hereinafter to any rough stones or half-processed stones before processing, e.g., such as for determining the rough gemstone value before purchasing it or for planning the subsequent process stages; in the gemstone processing stages, e.g., following the cleaving, sawing, bruting, and/or polishing stages; or after these preparation processes such as for evaluating the quality and value of the product produce thereof. The term specifically refers to rough stones, which provide diamonds and other precious or semi-precious gemstones.

The term 'inclusion' refers to internal and/or external features, which are wholly or partially surrounded by the stone, for instance, crystalline and solid inclusions, dot-like inclusions, flaws, clouds, clarity affecting phenomena, cracks, cleavage, fracture, tension, feather-like structural phenomena, or any combination thereof.

The term 'emitter' in the context of the present invention generally relates to any irradiation delivery device, including inter alia light source or a plurality of light sources emitting either visible light, white or monochromatic beam; and/or invisible light, including infra-red emission (IR), either in the near range or far range, and ultra-violet emission (UV) either in the near range or far range. The term also refers hereinafter to an X-ray radiation source and/or collimator of the same; a nucleic magnetic resonance (NMR), NQR, CT and/or MRI scatter; beta radiation emission devices; gamma radiation emission devices; laser beam cannons; photons cannons; microwave or RF emitters, etc. This term further refers to ultra-sound emitters, sonic or ultrasonic emitters or any combination thereof The term 'detector' in the context of the present invention refers to any sensor device adapted to detect the radiation delivered by the aforesaid emitter. The detector is adapted to detect said emitted radiation, a mixture thereof or a plurality of emissions, either directly or indirectly, e.g., through an interpreter. Such an interpreter may be selected from phosphorescent surface or the like. The detection according to the present invention is performed either on a single plane or a plurality of tangent planes, such as those assembled in a polygonal, hive-like, convex and/or concave configuration. The detection may be qualitative e.g., indicating in 0/1 fashion hit or miss of a predetermined measure of radiation on a predefined detecting pixel; or quantitative, e.g., fractional indication of the irradiation percentage detected in a given area or a particular detecting pixel. Moreover, the aforesaid emission may be amplified prior to detection or filtered, for instance through a filter adapted to lower noise-to-signal ratio, such as any standard Fourier Transform (FT) module and/or by a means of either a stationary or rotating grid adapted to screen back-scattered radiation.

The present invention generally relates to a non-destructive method of scanning the contour of a gemstone, while coordinating a well-defined three-dimensional (3D) position of one or more inclusions inside said gemstone. This novel method comprises inter alia the step of placing the gemstone to be examined on a rotatable holder, rotating it to a predetermined angle while emitting irradiation on said scanned gemstone. Concurrently or subsequently, at least one detector is used for detecting the emitted irradiation after scattering thereof, such that a two-dimensional in-scan of the gemstone is obtained. This process is repeated for a plurality of predetermined angles. Finally, a processor integrates the obtained multiple two-dimensional in-scans into a comprehensive three dimensional model of the gemstone's inner and/or outer portions, positioning the exact three dimensional location of inclusions therein.

It is acknowledged in this respect that a plurality of predetermined angles is provided by rotating the stone, the emitter or the detector, or by any combination thereof. Nevertheless, for sake of simplicity in the description, only one possible system, i.e., a system in which the gemstone rotates while both the emitter and the detector are immobilized to their initial place, is described and defined. Hence, it is according to one embodiment of the present invention wherein the step of rotating the gemstone by the holder is performed synchronously with the irradiation emitting, wherein the emission is provided in pulses or, alternatively, in a continuous movement, emission and/or detection.

According to a general embodiment of the present invention, the displacement is preferably provided by rotating the scanned gemstone by circulating the holder along a predetermined plane to a predetermined angle. For imaging the inner and/or outer portions of the gemstone, the gemstone is rotated in an overall rotation angle of about 45° to about 360° or more wherein images are taken in intervals of about 1° to about 10° or more. For imaging and or locating the inclusions, the gemstone is rotated in an overall rotation angle of about 45° to about 360° or more, wherein images are taken either in relatively large intervals, e.g., 3 to 8 images per overall rotation angle (e.g., intervals of 45° to 120°), in any predetermined intervals as function of the inclusion specific geometry or in small intervals, of about 1° to about 10° or more.

Said circular rotation is provided hereinafter along a single XY plane; however rotating and/or displacing the gemstone along a plurality of planes (e.g., XZ, YZ or XYZ) is a technology that may be easily achieved by those are skilled in the art.

Reference is made now to FIG. 1, presenting a schematic view of one embodiment of the aforesaid novel non-destructive analyzing system, providing for a well-defined three dimensional coordination map of inclusions in a gemstone in respect to said gemstone's external contours.

The system comprises a rotatable holder (1), such as a carrying dop or circular plate adapted for synchronized rotation (e.g., direction 1B) of a gemstone (6) to be scanned when placed thereon. Gemstone (6) is characterized by a boundary portion (e.g., the left rim of contour 6A), and potentially at least one internal or external inclusion (6B). A processor (2) activates a rotation mechanism (1A) of holder (1), such that it circulates it to a predetermined measure (e.g., 1 to 5 degrees), or activates it in a given time to a predetermined location. At least one emitter (3) provides an effective emission targeted towards the gemstone (6). Emitter (3) is also coupled with the processor (2), such that at any time its emission is triggered, regulated, or at least recorded. At least one detector (5) is designed for recording the emitted radiation after striking gemstone (6) at its inner and/or external portions. Detector (5) is also in online or offline communication with the processor (2). In case of X-ray emission, yet not restricted to such an example, at least one grid (4) is positioned between the gemstone and the detector to eliminate scattering and thus increase detection selectivity. Such a grid is either static or activated by a striking movement. Such a rotating grid is selected in a non-limiting manner from bucky grid actuators, rotating grids, cell-like grids, active grids adapted to emit visible or other invisible light etc. The system further comprises an output projecting means (7) such as a screen, data file etc., adapted to project the processed and stored 3D coordinated gemstone diagram.

The holder (1) rotation is synchronized by the processor (2) with the activation of the emitter (3), wherein the emission is provided. Detector (5) is further adapted to provide with the time t' of the emission detection at a given point, in reference to a time frame $t_0$ when the emission was emitted, thus allowing processor (2) efficiently to integrate the two-dimensional in-scans into a three-dimensional model.

It is in the scope of the present invention wherein emitter (3) radiates either a focused or unfocused beam onto the gemstone. For example, in accordance with a preferred embodiment of the invention, the aforesaid emitter, in combination with a commercially available collimator provides a substantially parallel beam of X-rays. Such a radiation is either provided in a series of pulses, in processed intervals or continuously. As a result, an X-ray beam illuminates both the perimeter of the gemstone, such as its left edge (6A), and any internal inclusion (such as flaw 6B). The incident beam is at least partially scattered towards the detector (5), in this example, a single commercially available X-ray detector. The radiation emitted towards the external perimeter (6A) propagates to the grid (4) (see dashed arrow 8A) and then to the detector (8C1). Radiation emitted towards the inclusion (6B) partially propagates directly to the grid (4) without changing a direction and then to the detector (8C2), or is partially scattered (see dashed arrow 8D) to the grid (4), where the scattered radiation is blocked from reaching the detector (see dashed arrow 8E).

Following this example, it is acknowledged that solid-state detectors for digital X-ray imaging are currently available commercially. These hybrid detectors incorporate inter alia CCDs with phosphor layers. Hence for example, U.S. Pat. No. 6,069,361 to Rubinstein of Eastman Kodak Co. discloses a high-resolution solid-state detector for use in a digital X-Ray imaging system. This detector includes two or more silicon CCDs, sandwiched together with phosphor screens or layers between them, in order to improve the overall sensitivity of the detector to X-rays. U.S. Pat. No. 6,775,348 to Hoffman of General Electric Company teaches a visual detector comprising a scintillator with built-in gain for receiving and converting high frequency electromagnetic energy to light in CT scanners. The terms 'CCD' or 'visual detectors' thus refer hereinafter to a video camera, an electronic camera, a digital camera, a digital video camera, hollow fibers and/or any other imaging device, possessing in a non-limiting manner concave, convex, non-zoom, zoom lenses or any combination thereof.

Hence grid (4) is designed according to one particulate embodiment of the present invention such that it emits phosphorus light in those pixels that a sufficient radiation is provided thereon. Referring again to FIG. 1, X-rays 8A or 8B are translated into visible or other light beams 8C1 or 8C2, respectively, wherein said light beams are detected by means of a CCD or any other visual detector (5). The detector is thus comprised of an array of pixels or has a continuous detecting surface. Moreover, such a process of rotating while emitting and detecting may be at least partially continuous or discontinuous, and may be provided either manually or automatically, e.g. by a computer-mediated means.

Reference is made now to FIGS. 2A-2C, schematically illustrating a rough gemstone containing an elongated blister-like small flaw, as detected by the aforesaid novel system. FIG. 2A presents a scanned lateral view (20) of the gemstone underlined in respect to non-scattered area (23), in an axis of 0 degrees (i.e., any initial point of view). The gemstone is found to comprise an irregular external contour (21A) and a substantially rectangular inner inclusion (22A). FIG. 2B presents the scanned gemstone in its extreme face view, at 90 degrees view, showing said cloud-like gemstone (21B) containing only one flaw with a circular cross-section. Moreover, said inner screening shows that the inclusion is located in a somewhat laterally remote portion of the gemstone, such that the stone's potential economical worth is not necessarily diminished. FIG. 2C presents the calculated 3D inner and outer gemstone view (21C) comprising a tubular inclusion (22C) presented at well-defined XYZ coordinates.

Reference is made now to figures, schematically presenting a top view of an imaging system according to yet another embodiment of the present invention, especially adapted for the location of inclusions in a gemstone. This system comprising inter alia a multiple sets of emitters and detectors. Here, one set is adapted to provide a 3D imaging the outer contour of the gemstone and a second set is adapted to provide either 2D or 3D mapping of the inclusions. Other systems are possible, as such imaging assemblies comprising X-ray means for radiating the gemstone such that a phosphorescent radiation interpreter radiates a invisible light; means for emitting a laser radiation towards said towards the interpreter or detector such that a visible image is detectable; wherein the laser-means and/or detectors thereof are adapted for particulate (e.g., pixel like) detection, or an overall real time detection of the laser-radiated surface.

What is claimed is:

1. A non-destructive method of testing a gemstone, said method comprising the steps of:
    a. providing an X-ray non-destructive system for obtaining a model of a gemstone comprising:
        i. a holder adapted to carry said gemstone,
        ii. at least one emitter adapted to provide an X-ray beam directed to said gemstone,
        iii. at least one detector adapted to detect the said beam passed through said gemstone,
        iv. displacing means adapted to displace said gemstone relative to said beam in a predetermined manner,
        v. a processor adapted to process and display said detected data such that a two-dimensional topographic pattern of said gemstone is obtained,
    said system further comprises a spatial filtering device, said device comprises comprising a plurality of plane elements arranged parallel to a non-scattered beam and is adapted so as to block said rays that are scattered by inclusions accommodated by in said gemstone and angularly propagated towards said detector;
    b. placing said gemstone on a said holder such that said gemstone to be tested is located in a path of said beam;
    c. passing said beam through said gemstone;
    d. radiating said gemstone by means of said emitter;
    e. scattering said beam on at least one inclusion accommodated in said gemstone;
    f. detecting said radiation passed through said gemstone by means of said detector; and
    g. processing said detection data produced in the step (f) such that said two-dimensional topographic pattern of said gemstone is obtained by means of said processor;
    wherein said method further comprises a step of filtering said scattered radiation out of said radiation passed through said gemstone.

2. The method according to claim 1, wherein said step of radiating said gemstone further comprises the emitting an X-ray radiation and collimating said radiation into substantially parallel beam.

3. The method according to claim 1, wherein the gemstone is tested at a stage of the gemstone processing procedure selected from the group consisting of (a) preliminary testing before processing procedure, (b) intermediate testing of a semi-processed gemstone after cleaving, sawing, bruting, and/or polishing and (c) final testing of the finished gemstone to evaluate quality and price of said gemstone.

4. The method according to claim 1, wherein said step of detecting said passed radiation is performed in a direct manner.

5. The method according to claim 4, wherein said step of detecting said passed radiation further comprises converting X-rays into visible light.

6. The method according to claim 5, wherein said step of converting X-rays into visible light is performed by projecting said X-rays onto a phosphorescent radiating surface.

7. The method according to claim 4, wherein said step of detection detecting of said emitted passed radiation comprises a further step selected from the group consisting of at least partially qualitatively evaluating an obtained detected signal, quantitatively evaluating said signal, amplifying said signal, filtering said signal, or and any combination thereof.

8. The method according to claim 1, comprising a step of displacing, said step further comprises rotating said tested gemstone in a predetermined plane about a predetermined angle.

9. The method according to claim 1, wherein said steps of radiating said tested gemstone by said X-rays and detecting said X-rays passed through said tested gemstone by said detector are followed by displacing said tested gemstone according to a predetermined protocol.

10. The method according to claim 1, wherein said method further comprises the steps of:
    a. displacing said gemstone relative said beam;
    b. repeating said steps b-g for a plurality of incident angles differing from each other by a predetermined value; and
    c. synthesizing a three-dimensional model of said gemstone based on said obtained two-dimensional topographic patterns.

11. The method according to claim 1, wherein said step of detecting said passed radiation is performed in an indirect manner.

12. An X-ray non-destructive system for obtaining either a model of a gemstone comprising:
    a. a holder adapted to carry a gemstone;
    b. at least one emitter adapted to provide an X-ray beam directed to said gemstone;
    c. at least one detector adapted to detect said beam passed through said gemstone;
    d. a displacing means adapted to displace said gemstone relative to said beam in a predetermined manner;
    e. a processor adapted to process and display said detected data such that a two-dimensional topographic pattern of said gemstone is obtained;
    wherein said system further comprises a spatial filtering device comprising a plurality of plane elements that are arranged in parallel to rays of a non-scattered beam that is propagated through said gemstone without changing the direction of the propagation such that said plane elements block rays scattered by gemstone inclusions which are angularly propagated to said detector.

13. The system according to claim 12, wherein said gemstone is selected from the group consisting of a rough precisions gemstone, a rough semi-precious gemstone, a semi-processed article made of multiple gemstones, and a finished article made of multiple gemstones.

14. The system according to claim 10, wherein said processor is adapted to integrate the obtained multiple the two-dimensional topographic patterns produced by said processor into a three-dimensional model of said gemstone.

15. The system according to claim 10, wherein said detector is a sensing device adapted to detect the radiation delivered by said emitter in an indirect manner.

16. The system according to claim 12, wherein said detector is a sensing device adapted to detect the radiation delivered by said emitter in a direct manner.

17. The system according to claim 16, wherein the detector further comprises at least one converter adapted to convert said X-rays into visible light.

18. The system according to claim 17, wherein the said converter further comprises a phosphorescent radiating surface.

19. The system according to claim 16, wherein said detector further comprises a matrix of detecting elements adapted for detection detecting radiation, and said detector is operable of operations selected from the group consisting of qualitative evaluation of an obtained detected signal, quantitative evaluation of said signal, amplification of said signal, filtration of said signal, and any combination thereof.

20. The system according to claim 12, wherein said displacing means is adapted for rotating the tested gemstone in a predetermined plane about a predetermined angle.

21. The system according to claim 12, wherein said processor is adapted to alternate radiating said tested gemstone by said X-rays, detecting said X-rays passed through said tested gemstone and displacing said tested gemstone according to a predetermined protocol.

22. The system according to claim 12, wherein said emitter is adapted to provide radiation pulses synchronized with said detector.

23. The system according to claim 12, wherein said emitter further comprises an X-ray source adapted to generate X-rays and a collimator adapted to convert said rays into substantially parallel beam.

* * * * *